United States Patent [19]

Meier

[11] Patent Number: 5,371,281
[45] Date of Patent: Dec. 6, 1994

[54] PROCESS FOR PREPARING ALKALI METAL 3-SULFOBENZOATES

[75] Inventor: Michael Meier, Frankfurt, Germany

[73] Assignee: Hoechst AG, Frankfurt, Germany

[21] Appl. No.: 103,409

[22] Filed: Aug. 6, 1993

[30] Foreign Application Priority Data

Aug. 7, 1992 [DE] Germany .................... 4226130

[51] Int. Cl.$^5$ .......................... C07C 309/29
[52] U.S. Cl. ............................ 562/56
[58] Field of Search ................... 562/56

[56] References Cited

U.S. PATENT DOCUMENTS 4,358,410 11/1982 Demler et al. .
4,393,234 7/1983 Blank et al. .
5,136,043 8/1992 Meier et al. .

OTHER PUBLICATIONS

Advanced Organic Chemistry, "Reactions, Mechanisms, and Structure", 3rd Edition, Jerry March, p. 444, Reaction O-117, 1974.
Gilbert, E. E., et al, *Ind. a. Eng. Chem.* vol. 45:2065–2071 (1953).

Primary Examiner—Nicky Chan
Attorney, Agent, or Firm—Connolly & Hutz

[57] ABSTRACT

The present invention relates to a process for preparing alkali metal 3-sulfobenzoates. 3-(Chlorosulfonyl)benzoic acid is admixed with an aqueous alkali metal chloride solution, the mixture is heated and, after reaction, cooled to ≦15° C. and the crystallized alkali metal 3-sulfobenzoate is separated off.

20 Claims, No Drawings

PROCESS FOR PREPARING ALKALI METAL 3-SULFOBENZOATES

The present invention relates to a process for preparing alkali metal 3-sulfobenzoates, distinguished from the prior art by a reduced production of effluent.

From Offermann, Liebigs Annalen der Chemie 280, 6 (1894), it is known that the sodium salt of 3-sulfobenzoic acid can be prepared by sulfonating benzoic acid with oleum at 200° C., pouring the resultant reaction product into a water-ice mixture and adding sodium chloride. A disadvantage of this process is that a dilute, sodium chloride-containing sulfuric acid is obtained, which can be worked up industrially only with great effort. Because of the high sodium chloride content the reaction product contains only 75% of the sodium salt of 3-sulfobenzoic acid.

In the process described in U.S. Pat. No. 4,358,410 benzoic acid is reacted with oleum at 130° C. and the reaction mixture obtained is subsequently admixed with a concentrated aqueous sodium chloride solution and cooled. This does lead to an improved purity of the product, but also to a large proportion of dilute sulfuric acid contaminated with sodium chloride, which is difficult to dispose of.

In a process described by Ruggli and Grün in Helv. Chim. Acta 24, 197 (1941) free 3-sulfobenzoic acid is obtained by reaction of 3-(chlorosulfonyl)benzoic acid with a 10-fold quantity of water while heating. Subsequently the water is distilled off, whereupon a syrup is obtained. This syrup is admixed with fresh water and the water subsequently distilled off again. This procedure is repeated twice. The disadvantage of this process is that three times large amounts of water, which cannot be used again, have to be distilled off. This requires a very high energy consumption. In addition, industrial implementation is only possible with difficulty, as 3-sulfobenzoic acid remains in the reaction vessel, which solid melts at 150° C. and therefore can only be removed from the reaction vessel as a hot melt. DE 3 122 264 and Ind. Eng. Chem. 45, 2065 (1953) relate to a process for preparing 3-sulfobenzoic acid by reaction of benzoic acid with the stoichiometric amount of sulfur trioxide. Here too, however, the solid product remaining in the reactor can only be removed in liquid melt form. This requires an increased technical effort and leads to problems in further processing. In addition, the handling of sulfur trioxide is not simple and requires special precautions.

There is therefore a need for a process which not only is simple to carry out technically, but also leads to a lowering of the amount of effluent. It should furthermore ensure that the desired product is obtained both in high yield and in high purity.

This object is achieved by a process for preparing alkali metal 3-sulfobenzoates, which comprises mixing 3-(chlorosulfonyl)benzoic acid with an aqueous alkali metal chloride solution, heating the mixture and, after reaction, cooling to $\leq 15°$ C. and separating off the crystallized alkali metal 3-sulfobenzoate.

The starting material 3-(chlorosulfonyl)benzoic acid can be prepared, for example, by the process described in DE 3 919 840. It can advantageously be used while moist with water. Its water content is usually from 20 to 40% by weight.

The alkali metal chloride used is sodium chloride or potassium chloride, in particular sodium chloride.

The aqueous solution should contain sufficient alkali metal chloride. Usually an aqueous solution containing from 15 to 30, in particular from 18 to 28 and preferably from 22 to 27% by weight of alkali metal chloride is used.

If sodium chloride is used as the alkali metal chloride, then the aqueous solution employed usually contains from 22 to 26.4% by weight of sodium chloride. Solutions with a lower sodium chloride content can also be used, but result in a correspondingly lower yield of sodium 3-sulfobenzoate and a correspondingly higher proportion of effluent. More concentrated sodium chloride solutions may, because of the solubility of sodium chloride in water, lead to difficulties in handling.

The amount of the aqueous alkali metal chloride solution is to a certain extent also dependent on the alkali metal chloride concentration of the solution.

Normally from 0.5 to 10, in particular from 0.7 to 4, preferably from 0.8 to 2.5 parts by weight of aqueous alkali metal chloride solution, in particular sodium chloride solution, are used per part by weight of 3-(chlorosulfonyl)benzoic acid.

The 3-(chlorosulfonyl)benzoic acid is thoroughly mixed with the aqueous alkali metal chloride solution and the resulting mixture is heated. Generally a reaction temperature of 80° C. suffices. This ensures a sufficiently fast reaction rate. It has also proved useful to employ a reaction temperature between 80° C. and the respective boiling point of the reaction mixture, in particular between 90° C. and the respective boiling point of the reaction mixture. Lower temperatures can also be used, but account must be taken of the fact that the reaction times will be extended. Higher temperatures do indeed favor the reaction rate, but may require the reaction to be carried out under pressure.

After completion of the reaction the reaction mixture is cooled. The final temperature of the cooling procedure should be $\leq 15°$ C. The cooling can be carried out in one step or divided into two steps.

It has been established that it is often advantageous to carry out the cooling in two steps, where initially, in a first step, the temperature is reduced to from 60° to 40° C., in particular from 50° to 40° C., and subsequently reduced to the final temperature of $\leq 15°$ C. Owing to the solubility of the alkali metal 3-sulfobenzoate in water, the final temperature of the cooling procedure also determines the product yield to a certain extent. To favorably influence the yield, a temperature below 15° C., in particular $\leq 10°$ C. and preferably $\leq 5°$ C., is desirable.

After the cooling is complete, the crystallized alkali metal 3-sulfobenzoate, in particular sodium 3-sulfobenzoate, is separated off, for example by filtration. For further purification it is desirable to wash the isolated crystals with an aqueous alkali metal chloride solution. Here an aqueous potassium chloride solution is used in the case of potassium 3-sulfobenzoate and a sodium chloride solution in the case of the sodium 3-sulfobenzoate.

The aqueous washing solution of alkali metal salt usually contains from 1 to 10%, in particular from 3 to 8% by weight of alkali metal chloride, preferably sodium chloride. The solution is advantageously cooled to a temperature $\leq 15°$ C., in particular $\leq 10°$ C., preferably $\leq 5°$ C. prior to use in the washing procedure.

The amount of washing solution to be used depends to a certain extent on the concentration and temperature of the alkali metal chloride solution employed. It has been found that usually from 0.3 to 2.5, in particular from 0.5 to 2 parts by weight of washing solution suffice per part by weight of 3-(chlorosulfonyl)benzoic acid originally used.

It is surprising that in the process of the invention the alkali metal 3-sulfobenzoate is formed directly by reaction of 3-(chlorosulfonyl)benzoic acid with the alkali metal chloride, without an addition of alkali metal hydroxide being necessary. An advantage of the process of the invention compared with the prior art is that firstly only small amounts of effluent are produced, which secondly have only a low sodium chloride content. The product is obtained in a high yield and contains only minor amounts of alkali metal chloride. In this way sodium 3-sulfobenzoate is formed in yields >90%, and contains less than 5% by weight of sodium chloride.

A further advantage of the process of the invention lies in the reusability of both the filtrate from the reaction of 3-(chlorosulfonyl)benzoic acid and the alkali metal chloride solution used as the washing solution. Hence the filtrate can, if desired, be topped up to the required amount with used washing solution, with the pH being adjusted if necessary to from 3 to 8, in particular from 4 to 6, by addition of alkali metal hydroxide, alkali metal hydrogen carbonate and/or alkali metal carbonate to neutralize any hydrochloric acid still present. The filtrate treated in this way can be used in a further batch. Thereby the amount of aqueous alkali metal chloride solution produced as effluent per batch is reduced.

The following examples illustrate the invention without limiting it.

EXPERIMENTAL PART

EXAMPLE 1

Preparation of sodium 3-sulfobenzoate 360 g of 26.4% strength sodium chloride solution, prepared from 95.0 g of sodium chloride and 265.0 g of water, and 332 g of crude 3-(chlorosulfonyl)benzoic acid (water content: 39.2%) (corresponding to 201.8 g (0.92 mol) of 100% 3-(chlorosulfonyl)benzoic acid) are introduced into a 1 l four-neck flask fitted with stirrer, internal thermometer and reflux condenser. The reaction mixture is heated to 100° C. and stirred for a further 45 minutes at this temperature. The mixture is then allowed to cool over about 1 hour to 40° C. Subsequently it is cooled with an ice bath to <5° C. and stirred for a further 30 minutes at this temperature. The precipitated product is filtered off with suction and washed with 256 g of 5% strength sodium chloride solution, prepared from 12.8 g of sodium chloride and 243.2 g of water and cooled to 5° C., in two portions. The filter cake is dried at 100° C./100 torr (13.16 kPa). 196.3 g of sodium 3-sulfobenzoate are obtained with a purity of 95% and a sodium chloride content of 3.9% (corresponding to 186.5 g (0.83 mol) of 100% sodium 3-sulfobenzoate). The yield is 90.9% of theoretical. 345 g of mother liquor and 318 g of wash liquor are produced.

EXAMPLE 2

Preparation of sodium 3-sulfobenzoate 600 g of 26.4% sodium chloride solution and 290 g of crude 3-(chlorosulfonyl)benzoic acid (water content: 29.9%) (corresponding to 203.3 g (0.92 mol) of 100% 3-(chlorosulfonyl)benzoic acid) are introduced into a 2 l four-neck flask fitted with stirrer, internal thermometer and reflux condenser. The reaction mixture is heated to 100° C. and stirred for a further 1 hour at this temperature. The mixture is then allowed to cool over about 1 hour to 40° C. Subsequently it is cooled with an ice bath to <5° C. and stirred for a further 30 minutes at this temperature. The precipitated product is filtered off with suction and washed with 180 g of 5% strength sodium chloride solution cooled to 5° C., in 4 portions. The filter cake is dried at 100° C./100 torr (13.16 kPa). 200.0 g of sodium 3-sulfobenzoate are obtained with a purity of 94.5% and a sodium chloride content of 4.1%, which corresponds to 189.0 g (0.84 mol) of sodium 3-sulfobenzoate calculated as 100%. The yield is 91.5% of theoretical.

EXAMPLE 3

Preparation of sodium 3-sulfobenzoate with recycling of the mother liquor

The pH of 345 g of mother liquor from Example 1 is adjusted to 4 with about 60 g of sodium hydroxide. 300 ml of this solution are introduced together with 264.5 g of 3-(chlorosulfonyl)benzoic acid (water content: 25.7%) (corresponding to 196.5 g (0.89 mol) of 100% 3-(chlorosulfonyl)benzoic acid). The reaction mixture is heated to 100° C. and stirred for a further 45 minutes at this temperature. The mixture is then allowed to cool over about 1 hour to 40° C. Subsequently it is cooled with an ice bath to <5° C. and stirred for a further 30 minutes at this temperature. The precipitated product is filtered off with suction and washed with 256 g of 5% strength sodium chloride solution, prepared from 13.8 g of sodium chloride and 243.2 g of water and cooled to 5° C., in two portions. The filter cake is dried at 100° C./100 torr (13.16 kPa). 192.6 g of sodium 3-sulfobenzoate are obtained with a purity of 96% and a sodium chloride content of 3.2% (corresponding to 184.9 g (0.83 mol) of 100% sodium 3-sulfobenzoate). The yield is 92.6% of theoretical.

COMPARATIVE EXAMPLE 1

Preparation of sodium 3-sulfobenzoate according to U.S. Pat. No. 4,358,410

122.1 g (1.0 mol) of benzoic acid are melted at 125° to 130° C. in a 1 l four-neck flask fitted with stirrer, internal thermometer and reflux condenser. Then 405 g of oleum are introduced over 30 minutes. Subsequently the reaction mixture is heated to 130° C. and stirred for a further 1 hour at this temperature. The reaction mixture is cooled and 1800 g (=1500 ml) of 26.4% strength sodium chloride solution are run in over 15 minutes. The reaction mixture is heated to 80° C. to 85° C. Then the mixture is allowed to cool to 50° C. while stirring. Subsequently it is cooled with an ice bath to <5° C. and stirred for a further 30 minutes at this temperature. The precipitated product is filtered off with suction and washed with 256 g (=250 ml) of 5% strength sodium chloride solution cooled to 5° C., in two portions. After drying, 204.4 g of sodium 3-sulfobenzoate are obtained with a purity of 96% and a sodium chloride content of 3% (corresponding to 196.3 g (0.88 mol) of 100% sodium 3-sulfobenzoate). 2342 g of effluent are produced.

COMPARATIVE EXAMPLE 2

Preparation of 3-(chlorosulfonyl)benzoic acid according to DE 39 19 840, Example 16

349.5 g =199.7 ml (3.0 mol) of chlorosulfuric acid and 20.0 g of 96% strength sulfuric acid are placed in a 2 l four-neck flask fitted with stirrer, internal thermometer, reflux condenser with gas outlet and dropping funnel, at 25° C., and 1.0 g of sulfamic acid is added. Subsequently 122.1 g (1.0 mol) of benzoic acid are introduced into this mixture. The reaction mixture is heated to 120° C. over 3 hours and stirred further until evolution of HCl has ended (about 30 minutes). Then it is cooled to 70° C. and 119.0 g (1.0 mol) of thionyl chloride are added dropwise over 2 hours. The reaction solution is then heated to 80° C. and stirred further for about 30 minutes until gas evolution has ended. The mixture is added dropwise to 1000 g of ice-water at 10° C. over 2 hours. The precipitated product is filtered off with suction and washed with 500 g of ice-water. 321.2 g of crude 3-(chlorosulfonyl)benzoic acid (water content: 33.9%; chlorine: 10.8%), corresponding to 212.3 g (0.96 mol) of 100% 3-(chlorosulfonyl)benzoic acid. 1115 g of mother liquor and 538 g of wash-water are produced.

As the summarized comparative presentation in the following table shows, the combination of the process described in DE 39 19 840 with the process of the invention, when compared with the prior art represented by U.S. Pat. No. 4,358,410, leads not only to a reduction in the amount of effluent, but also to a lowering of the wastes contained in the effluent.

TABLE

Comparison of the amounts and contents of effluent produced in the preparation of 1 mol of sodium 3-sulfobenzoate, in each case starting with benzoic acid.

|  | 1*  Sodium 3-sulfobenzoate according to U.S. Pat. No. 4,358,410 | 2*  Chlorosulfonyl-benzoic acid according to DE 39 19 840 | 3*  NaCl hydrolysis according to Example 1 | 4*  Sum of 2* and 3* |
|---|---|---|---|---|
| Amount of effluent: containing | 2674 g | 1888 g | 382 g | 2270 g |
| $H_2SO_4$ | 371 g | 247 g | — | 247 g |
| NaCl | 476 g | — | 40 g | 40 g |
| HCl | 41 g | 83 g | — | 83 g |

1* = Comparative Example 1;
2* = Comparative Example 2;
3* = Example 1;
4* = Sum of 2* and 3*.

What is claimed is:

1. A process for preparing alkali metal 3-sulfo-benzoate, which comprises admixing 3-(chlorosulfonyl)benzoic acid with an aqueous alkali metal chloride solution, heating the mixture and, after reaction, cooling to less than or equal to 15° C. and separating off the crystallized alkali metal 3-sulfobenzoate.

2. The process as claimed in claim 1, wherein the alkali metal chloride is sodium chloride or potassium chloride.

3. The process as claimed in claim 1, wherein the aqueous solution contains from 15 to 30% by weight of alkali metal chloride.

4. The process as claimed in claim 1, wherein the aqueous solution contains from 22 to 26.4% by weight of sodium chloride.

5. The process as claimed in claim 1, wherein from 0.5 to 10 parts by weight of aqueous alkali metal chloride solution are used per part by weight of 3-(chlorosulfonyl)benzoic acid.

6. The process as claimed in claim 1, wherein the mixture is heated to a temperature of from 80° C. to the boiling point of the mixture.

7. The process as claimed in claim 1, wherein the mixture after reaction is cooled firstly to from 60° to 40° C. and subsequently to less than or equal to 15° C.

8. The process as claimed in claim 1, wherein the alkali metal 3-sulfobenzoate is washed with an aqueous solution containing from 1 to 10% by weight of alkali metal chloride and having a temperature of less than or equal to 15° C.

9. The process as claimed in claim 1, wherein the aqueous alkali metal chloride solution produced, which has optionally its pH adjusted to from 3 to 8 by addition of alkali metal hydroxide, alkali metal hydrogen carbonate or alkali metal carbonate, is reused in the process.

10. The process as claimed in claim 2, wherein the alkali metal chloride is sodium chloride.

11. The process as claimed in claim 3, wherein the aqueous solution contains from 18 to 28 percent by weight of alkali metal chloride.

12. The process as claimed in claim 3, wherein the aqueous solution contains from 22 to 27 percent by weight of alkali metal chloride.

13. The process as claimed in claim 5, wherein from 0.7 to 4 parts by weight of aqueous alkali sodium chloride solution are used per part by weight of 3-(chlorosulfonyl)benzoic acid.

14. The process as claimed in claim 5, wherein from 0.8 to 2.5 parts by weight of aqueous alkali sodium chloride solution are used per part by weight of 3-(chlorosulfonyl)benzoic acid.

15. The process as claimed in claim 6, wherein the mixture is heated to a temperature of from 90° C. to the boiling point of the mixture.

16. The process as claimed in claim 7, wherein the mixture after reaction is cooled firstly to from 50° to 40° C. and subsequently to less than or equal to 10° C.

17. The process as claimed in claim 15, wherein the mixture is subsequently cooled to less than or equal to 5° C.

18. The process as claimed in claim 8, wherein the alkali metal 3-sulfobenzoate is washed with an aqueous solution containing from 3 to 8% by weight of alkali sodium chloride and having a temperature of less than or equal to 10° C.

19. The process as claimed in claim 18, wherein said temperature is less than or equal to 5° C.

20. The process as claimed in claim 9, wherein the pH is adjusted from 4 to 6.

* * * * *